(12) United States Patent
Kim (10) Patent No.: US 11,955,272 B1
(45) Date of Patent: Apr. 9, 2024

(54) METHOD FOR GENERATING OBJECT DETECTOR BASED ON DEEP LEARNING CAPABLE OF DETECTING EXTENDED OBJECT CLASS AND DETECTOR GENERATION DEVICE USING THE SAME

(71) Applicant: Superb AI Co., Ltd., Seoul (KR)

(72) Inventor: Kye Hyeon Kim, Suwon-si (KR)

(73) Assignee: SUPERB AI CO., LTD., Seoul (KR)

( * ) Notice: Subject to any disclaimer, the term of this patent is extended or adjusted under 35 U.S.C. 154(b) by 0 days.

(21) Appl. No.: 18/384,731

(22) Filed: Oct. 27, 2023

(30) Foreign Application Priority Data

Nov. 10, 2022 (KR) ........................ 10-2022-0149470

(51) Int. Cl.
*H01F 27/40* (2006.01)
*G01N 33/00* (2006.01)

(52) U.S. Cl.
CPC ....... *H01F 27/402* (2013.01); *G01N 33/0034* (2013.01); *H01F 2027/404* (2013.01)

(58) Field of Classification Search
CPC ............ H01F 27/402; H01F 2027/404; G01N 33/0034
See application file for complete search history.

(56) References Cited

U.S. PATENT DOCUMENTS

| | | | | |
|---|---|---|---|---|
| 10,303,981 | B1* | 5/2019 | Kim | G06F 18/2431 |
| 10,885,388 | B1* | 1/2021 | Kim | G06F 18/217 |
| 11,113,574 | B1* | 9/2021 | Ryu | G06N 3/045 |
| 2020/0334501 | A1* | 10/2020 | Lin | G06F 18/214 |
| 2021/0117717 | A1* | 4/2021 | Ha | G06N 20/00 |
| 2021/0150275 | A1* | 5/2021 | Schulter | G06V 20/58 |
| 2021/0326646 | A1* | 10/2021 | Gultekin | G06V 10/82 |
| 2023/0245422 | A1* | 8/2023 | Okada | G06V 10/809 |
| | | | | 382/156 |

* cited by examiner

*Primary Examiner* — Santiago Garcia
(74) *Attorney, Agent, or Firm* — Frost Brown Todd LLP; Alexander J. Johnson

(57) ABSTRACT

A method for generating an object detector based on deep learning capable of detecting an extended object class is provided. The method is related to generating the object detector based on the deep learning capable of detecting the extended object class to thereby allow both an object class having been trained and additional object class to be detected. According to the method, it is possible to generate the training data set necessary for training an object detector capable of detecting the extended object class at a low cost in a short time and further it is possible to generate the object detector capable of detecting the extended object class at a low cost in a short time.

18 Claims, 6 Drawing Sheets

METHOD FOR GENERATING OBJECT DETECTOR BASED ON DEEP LEARNING CAPABLE OF DETECTING EXTENDED OBJECT CLASS AND DETECTOR GENERATION DEVICE USING THE SAME

CROSS REFERENCE OF RELATED APPLICATION

This present application claims the benefit of the earlier filing date of Korean patent application No. 10-2022-0149470, filed on Nov. 10, 2022, the entire contents of which being incorporated herein by reference.

FIELD OF THE DISCLOSURE

The present disclosure relates to a method for generating an object detector based on deep learning and a detector generation device using the same; and more particularly, to the method for generating an object detector based on deep learning capable of detecting an extended object class to allow both an object class having been trained and additional object class to be detected.

BACKGROUND OF THE DISCLOSURE

Recently, research on a method for performing identification, etc. of an object using machine learning is being made. Deep learning using neural network having numerous hidden layers between an input layer and an output layer as one of such machine learning has a high performance in identification.

In addition, the neural network using the deep learning is generally trained through backpropagation using losses.

In order to proceed with training of such a deep learning network, training data annotated by labelers are necessary.

As one example, a deep learning-based object detector may collect images including one or more target objects corresponding to target object classes to be detected, generate training data set by annotation of the target object classes for the target objects in each of the collected images, and train the object detector by using the generated training data set, to thereby detect the target objects corresponding to the trained target object classes in new images.

Meanwhile, on condition that the object detector has been trained to detect the target objects for the target object classes, if there is a need to further detect new objects for new object classes, the object detector must be trained to further detect the new objects. For this purpose, a new training data set additionally annotated with the new object classes for the new objects are necessary.

However, previous images included in the training data set generated to be used for detecting the target objects are images collected for the target objects, and thus there are not many new objects corresponding to the new object classes in the previous images, and accordingly, there is a problem that it is difficult to train the object detector to additionally detect the new object classes in addition to the target object classes with just the previous training data set.

Accordingly, separate from the previous images collected for the target objects, new images should be collected for the new objects corresponding to the new object classes.

In addition, if the new images for the new objects are collected, the new object classes should be additionally annotated to the previous images where the target object classes have been annotated, and the target object classes and the new object classes should be annotated on the new images. Then the object detector is trained by using the new images and the previous images where the target object classes and the new object classes are annotated, to thereby generate an object detector capable of detecting an extended class set.

However, in such a conventional method, each of the previous images included in the previous training data set where the target object classes are annotated should be checked to annotate each of the new object classes corresponding to the new objects to each of the previous images. Further, the target objects and the new objects should be checked in each of the new images to annotate each of the target object classes and the new object classes.

Therefore, considerable times and considerable costs are required for the annotation to generate a new training data set having the extended object class.

SUMMARY OF THE DISCLOSURE

It is an object of the present disclosure to solve all the aforementioned problems.

It is another object of the present disclosure to easily generate a training data set having an extended object class.

It is still another object of the present disclosure to minimize an annotation cost for the extended object class.

It is still yet another object of the present disclosure to minimize an annotation time for the extended object class.

It is still yet another object of the present disclosure to generate the training data set necessary for training an object detector capable of detecting the extended object class at a low cost in a short time.

It is still yet another object of the present disclosure to generate the object detector capable of detecting the extended object class at a low cost in a short time.

In accordance with one aspect of the present disclosure, there is provided a method for generating an object detector based on deep learning for detecting an extended object class, comprising steps of: (a) on condition that a first object detector is generated, wherein the first object detector has been trained to detect one or more first objects in a first input image by using a first training data set generated by annotation of first object classes of the first objects in each of first source images containing at least one of the first objects, in response to acquiring second source images containing one or more second objects, a detector generation device generating a second training data set by annotation of second object classes of the second objects for each of the second source images, and generating a second object detector trained to detect the second objects in a second input image by using the second training data set; (b) the detector generation device (i) (i-1) inputting the first source images of the first training data set into the second object detector, thereby instructing the second object detector to detect the second objects contained in each of the first source images and thus to output second object detection results, and (i-2) generating a third training data set containing the first source images in which the first object classes and the second object classes are annotated by annotation of the second object classes for the second objects detected in each of the first source images by referring to the second object detection results, and (ii) (ii-1) inputting the second source images of the second training data set into the first object detector, thereby instructing the first object detector to detect the first objects contained in each of the second source images and thus to output first object detection results, and (ii-2) generating a fourth training data set containing the second source images in which the first object classes and the second object classes are annotated by annotation of the first object classes for the first objects detected in each of the second source images by referring to the first object detection results; and (c) the detector generation device generating an integrated object detector trained to detect the first objects and the second objects in a third input image by using the third training data set and the fourth training data set.

At the step of (a), the detector generation device may generate an object detector having initialized weights by initializing trained weights of the first object detector, and generates the second object detector by training the object detector having the initialized weights by using the second training data set.

At the step of (c), the detector generation device may generate the object detector having initialized weights by initializing trained weights of the first object detector or by initializing trained weights of the second object detector, and generates the integrated object detector by training the object detector having the initialized weights by using the third training data set and the fourth training data set.

At the step of (c), the detector generation device may generate the integrated object detector by re-training the first object detector using the third training data set and the fourth training data set.

At the step of (c), the detector generation device may generate the integrated object detector by re-training the second object detector using the third training data set and the fourth training data set.

Prior to the step of (a), the detector generation device may transmit the first images to one or more first labeler terminals to thereby instruct the first labelers corresponding to the first labeler terminals to annotate the first object classes for each of the first images and instruct the first labelers to transmit the first images having the first object classes annotated through the first labeler terminals to the detector generation device, resulting in a generation of the first training data set.

At the step of (a), the detector generation device may transmit the second images to one or more second labeler terminals to thereby instruct the second labelers corresponding to the second labeler terminals to annotate the second object classes for each of the second images and instruct the second labelers to transmit the second images having the second object classes annotated through the second labeler terminals to the detector generation device, resulting in a generation of the second training data set.

The first object detector, the second object detector and the integrated object detector may be generated by using an R-CNN-based object detector.

The first object detector, the second object detector and the integrated object detector may be generated by using an instance segmentation-based object detector.

In accordance with still another aspect of the present disclosure, there is provided a detector generation device for generating an object detector based on deep learning capable of detecting an extended object class, comprising: at least one memory that stores instructions; and at least one processor configured to execute the instructions to perform or support another device to perform processes of: (I) on condition that a first object detector is generated, wherein the first object detector has been trained to detect one or more first objects in a first input image by using a first training data set generated by annotation of first object classes of the first objects in each of first source images containing at least one of the first objects, in response to acquiring second source images containing one or more second objects, a detector generation device generating a second training data set by annotation of second object classes of the second objects for each of the second source images, and generating a second object detector trained to detect the second objects in a second input image by using the second training data set; (II) (i) (i-1) inputting the first source images of the first training data set into the second object detector, thereby instructing the second object detector to detect the second objects contained in each of the first source images and thus to output second object detection results, and (i-2) generating a third training data set containing the first source images in which the first object classes and the second object classes are annotated by annotation of the second object classes for the second objects detected in each of the first source images by referring to the second object detection results, and (ii) (ii-1) inputting the second source images of the second training data set into the first object detector, thereby instructing the first object detector to detect the first objects contained in each of the second source images and thus to output first object detection results, and (ii-2) generating a fourth training data set containing the second source images in which the first object classes and the second object classes are annotated by annotation of the first object classes for the first objects detected in each of the second source images by referring to the first object detection results; and (III) generating an integrated object detector trained to detect the first objects and the second objects in a third input image by using the third training data set and the fourth training data set.

At the process of (I), the processor may generate an object detector having initialized weights by initializing trained weights of the first object detector, and generates the second object detector by training the object detector having the initialized weights by using the second training data set.

At the process of (III), the processor may generate the object detector having initialized weights by initializing trained weights of the first object detector or by initializing trained weights of the second object detector, and generates the integrated object detector by training the object detector having the initialized weights by using the third training data set and the fourth training data set.

At the process of (III), the processor may generate the integrated object detector by re-training the first object detector using the third training data set and the fourth training data set.

At the process of (III), the processor may generate the integrated object detector by re-training the second object detector using the third training data set and the fourth training data set.

Prior to the process of (I), the processor may transmit the first images to one or more first labeler terminals to thereby instruct the first labelers corresponding to the first labeler terminals to annotate the first object classes for each of the first images and instruct the first labelers to transmit the first images having the first object classes annotated through the first labeler terminals to the detector generation device, resulting in a generation of the first training data set.

At the process of (I), the processor may transmit the second images to one or more second labeler terminals to thereby instruct the second labelers corresponding to the second labeler terminals to annotate the second object classes for each of the second images and instruct the second labelers to transmit the second images having the second object classes annotated through the second labeler terminals to the detector generation device, resulting in a generation of the second training data set.

The first object detector, the second object detector and the integrated object detector may be generated by using an R-CNN-based object detector.

The first object detector, the second object detector and the integrated object detector may be generated by using an instance segmentation-based object detector.

In addition, recordable media that are readable by a computer for storing a computer program to execute the method of the present disclosure is further provided.

BRIEF DESCRIPTION OF THE DRAWINGS

The accompanying drawings used to explain example embodiments of the present disclosure are only part of example embodiments of the present disclosure and other drawings can be obtained based on the drawings by those skilled in the art of the present disclosure without inventive work.

DETAILED DESCRIPTION OF THE PREFERRED EMBODIMENTS

The following detailed description of the present disclosure refers to the accompanying drawings, which show by way of illustration a specific embodiment in which the present disclosure may be practiced, in order to clarify the objects, technical solutions and advantages of the present disclosure. These embodiments are described in sufficient detail to enable those skilled in the art to practice the present disclosure.

Besides, in the detailed description and claims of the present disclosure, a term "include" and its variations are not intended to exclude other technical features, additions, components or steps. Other objects, benefits and features of the present disclosure will be revealed to one skilled in the art, partially from the specification and partially from the implementation of the present disclosure. The following examples and drawings will be provided as examples but they are not intended to limit the present disclosure.

Moreover, the present disclosure covers all possible combinations of example embodiments indicated in this specification. It is to be understood that the various embodiments of the present disclosure, although different, are not necessarily mutually exclusive. For example, a particular feature, structure, or characteristic described herein in connection with one embodiment may be implemented within other embodiments without departing from the spirit and scope of the present disclosure. In addition, it is to be understood that the position or arrangement of individual elements within each disclosed embodiment may be modified without departing from the spirit and scope of the present disclosure. The following detailed description is, therefore, not to be taken in a limiting sense, and the scope of the present disclosure is defined only by the appended claims, appropriately interpreted, along with the full range of equivalents to which the claims are entitled. In the drawings, like numerals refer to the same or similar functionality throughout the several views.

To allow those skilled in the art to carry out the present disclosure easily, the example embodiments of the present disclosure will be explained by referring to attached diagrams in detail as shown below.

Figure 1:
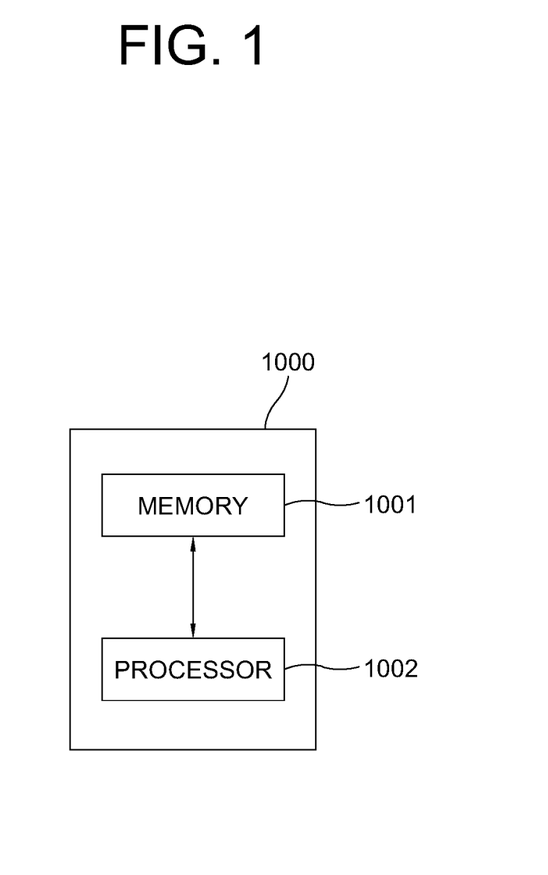
FIG. 1 is a drawing schematically illustrating a detector generation device for generating an object detector based on deep learning capable of detecting an extended object class in accordance with one example embodiment of the present disclosure.

FIG. 1 is a drawing schematically illustrating a detector generation device for generating an object detector based on deep learning capable of detecting an extended object class in accordance with one example embodiment of the present disclosure, and referring to FIG. 1, a detector generation device 1000 may include a memory 1001 that stores instructions for generating an object detector based on deep learning capable of detecting an extended object class; and a processor 1002 configured to perform operations for generating the object detector based on deep learning capable of detecting the extended object class in accordance with the instructions stored in the memory 1001.

Specifically, the detector generation device 1000 may achieve a desired system performance by using combinations of at least one computing device and at least one computer software, e.g., a computer processor, a memory, a storage, an input device, an output device, or any other conventional computing components, an electronic communication device such as a router or a switch, an electronic information storage system such as a network-attached storage (NAS) device and a storage area network (SAN) as the computing device and any instructions that allow the computing device to function in a specific way as the computer software.

The processor of the computing device may include hardware configuration of MPU (Micro Processing Unit) or CPU (Central Processing Unit), cache memory, data bus, etc. Additionally, the computing device may further include OS and software configuration of applications that achieve specific purposes.

However, the case in which the computing device includes an integrated processor, integrating a medium, a processor and a memory, for implementing the present disclosure is not excluded.

In addition, the processor 1002 of the detector generation device 1000 may perform processes of: on condition that a first object detector is generated, wherein the first object detector has been trained to detect one or more first objects in a first input image by using a first training data set generated by annotation of first object classes of the first objects in each of first source images containing at least one of the first objects, in response to acquiring second source images containing one or more second objects, (i) generating a second training data set by annotation of second object classes of the second objects for each of the second source images, and (ii) generating a second object detector trained to detect the second objects in a second input image by using the second training data set. Thereafter, the processor 1002 may perform processes of: (i) (i-1) inputting the first source images of the first training data set into the second object detector, thereby instructing the second object detector to detect the second objects contained in each of the first source images and thus to output second object detection results, and (i-2) generating a third training data set containing the first source images in which the first object classes and the second object classes are annotated by annotation of the second object classes for the second objects detected in each of the first source images by referring to the second object detection results, and (ii) (ii-1) inputting the second source images of the second training data set into the first object detector, thereby instructing the first object detector to detect the first objects contained in each of the second source images and thus to output first object detection results, and (ii-2) generating a fourth training data set containing the second source images in which the first object classes and the second object classes are annotated by annotation of the first object classes for the first objects detected in each of the second source images by referring to the first object detection results. In addition, the processor 1002 may perform a process of generating an integrated object detector trained to detect the first objects and the second objects in a third input image by using the third training data set and the fourth training data set.

Figure 2:
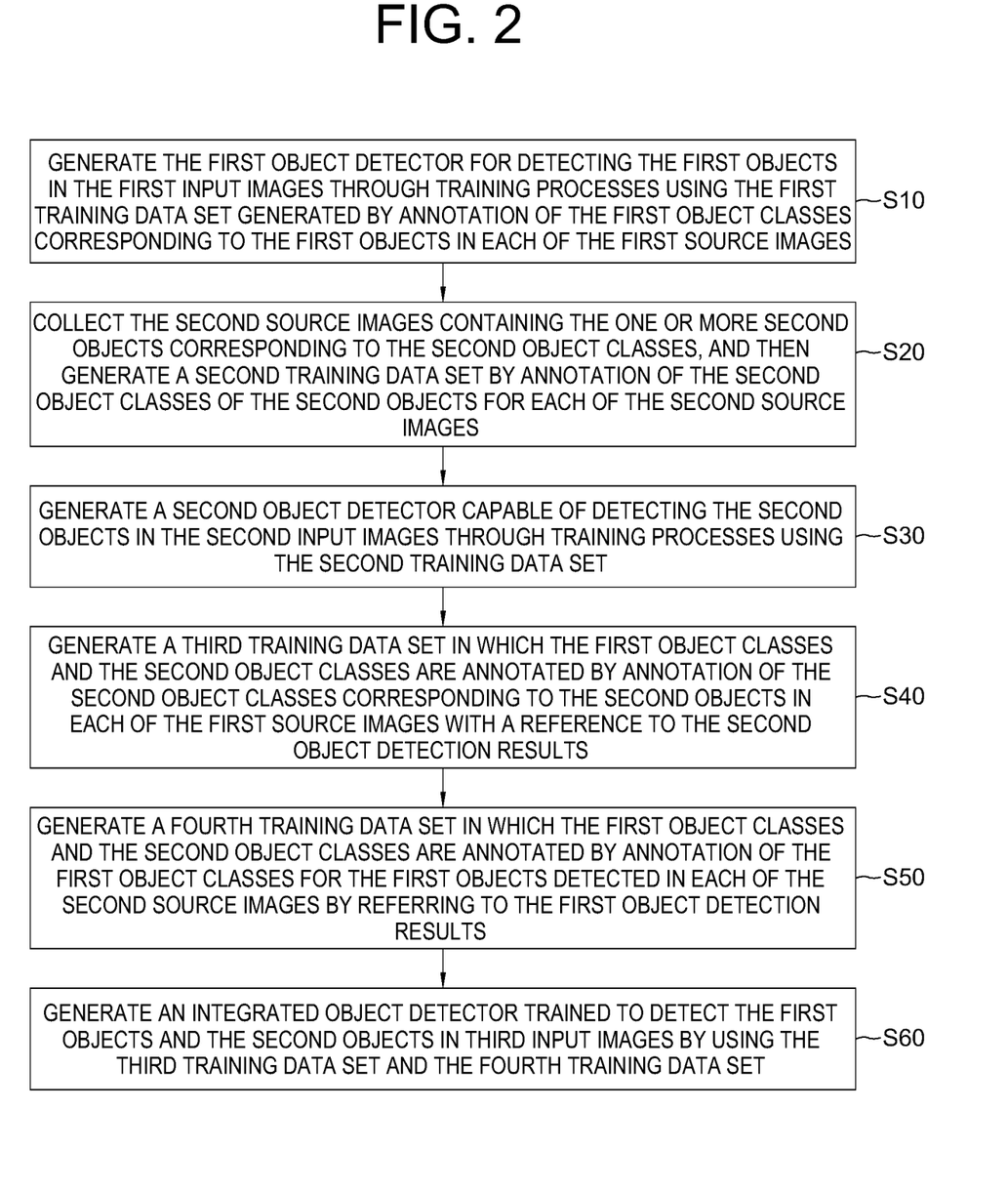
FIG. 2 is a drawing schematically illustrating the method for generating the object detector based on deep learning capable of detecting the extended object class in accordance with one example embodiment of the present disclosure.

A method for generating the object detector based on deep learning capable of detecting the extended object class using the detector generation device 1000 in accordance with one example embodiment of the present disclosure configured as above is explained by referring to FIG. 2 as follows.

Firstly, the detector generation device 1000 may generate the first object detector for detecting the first objects in the first input images through training processes using the first training data set generated by annotation of the first object classes corresponding to the first objects in each of the first source images at a step of S10. Herein, the first input images may be first images contained in the first training data set, or may be test images inputted to perform testing processes of the trained first object detector.

Figure 3:
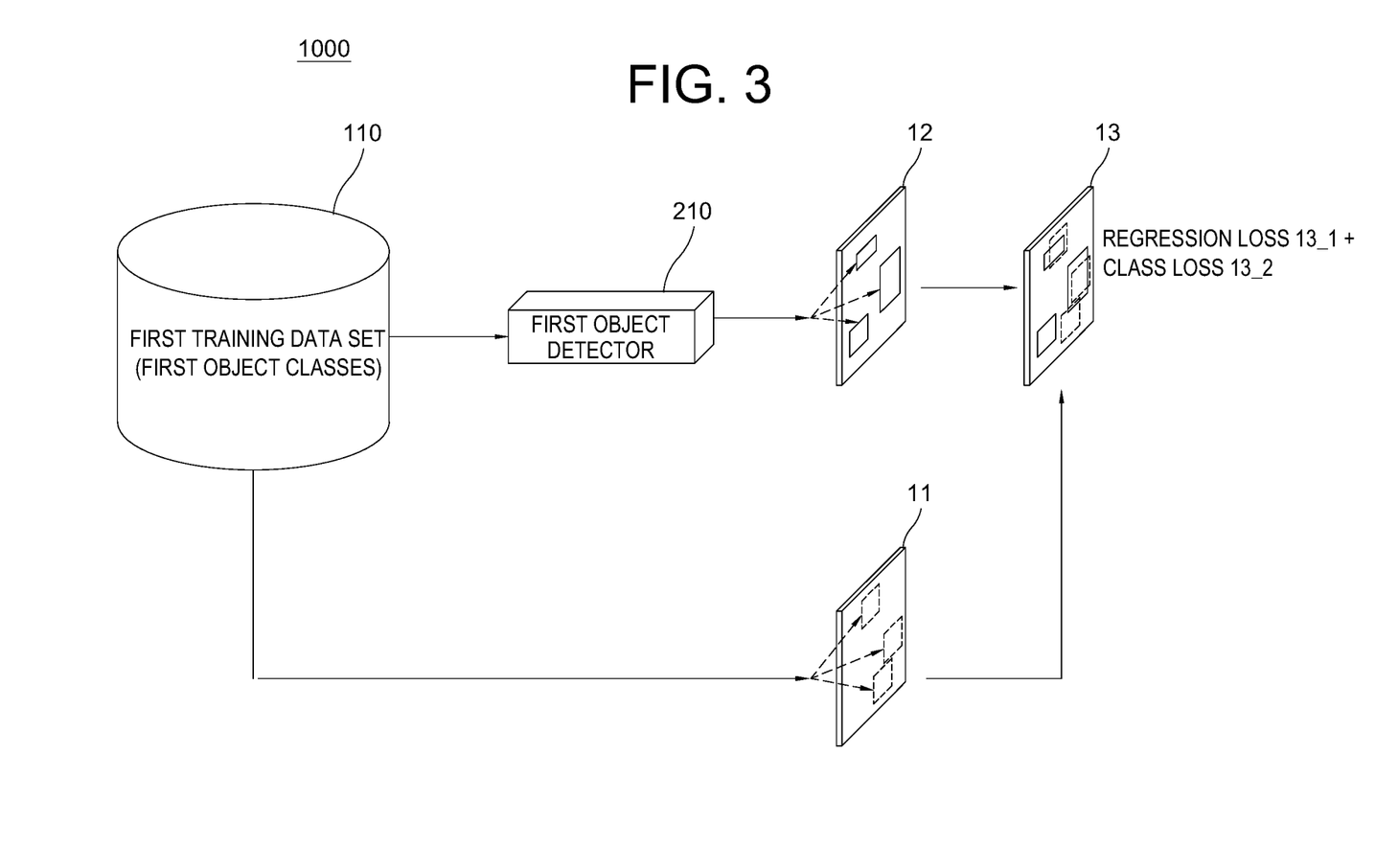
FIG. 3 is a drawing schematically illustrating a process of training a first object detector in the method for generating the object detector based on deep learning capable of detecting the extended object class in accordance with one example embodiment of the present disclosure.

As one example, the detector generation device 1000 collects the first source images including the one or more first objects to be used for training the first object detector, transmits the collected first source images to one or more terminals of first labelers to thereby instruct the first labelers to annotate the first object classes for each of the first source images and thus to generate a first training data set 110 as in FIG. 3 and instruct the first labelers to transmit the first training data set 110 having the first object classes annotated to the detector generation device 1000. Herein, in order to produce a good detection performance of the object detector, the first objects of sufficiently numerous n should be collected, and accordingly, in case an average number of the first objects included in each of the first source images is j, the number of the first source images to be collected should be n/j.

Referring to FIG. 3 again, the detector generation device 1000 may (i) input the first source images of the first training data set 110 to a first object detector 210 having initialized weights, to thereby instruct the first object detector 210 to detect the first objects corresponding to the first object classes in each of the first source images, (ii) acquire (ii-1) regression losses 13_1 regarding positions of bounding boxes and (ii-2) class losses 13_2 regarding object classes of the bounding boxes by using (1) object detection results 12 acquired by detecting the first objects in each of the first source images through the first object detector 210 and (2) ground truths 11 for the first object classes annotated in each of the first source images, and (iii) update weights of the first object detector 210 to minimize the regression losses 13_1 and the class losses 13_2 by backpropagating them, to thereby generate the first object detector 210 having first weights.

Figure 4:
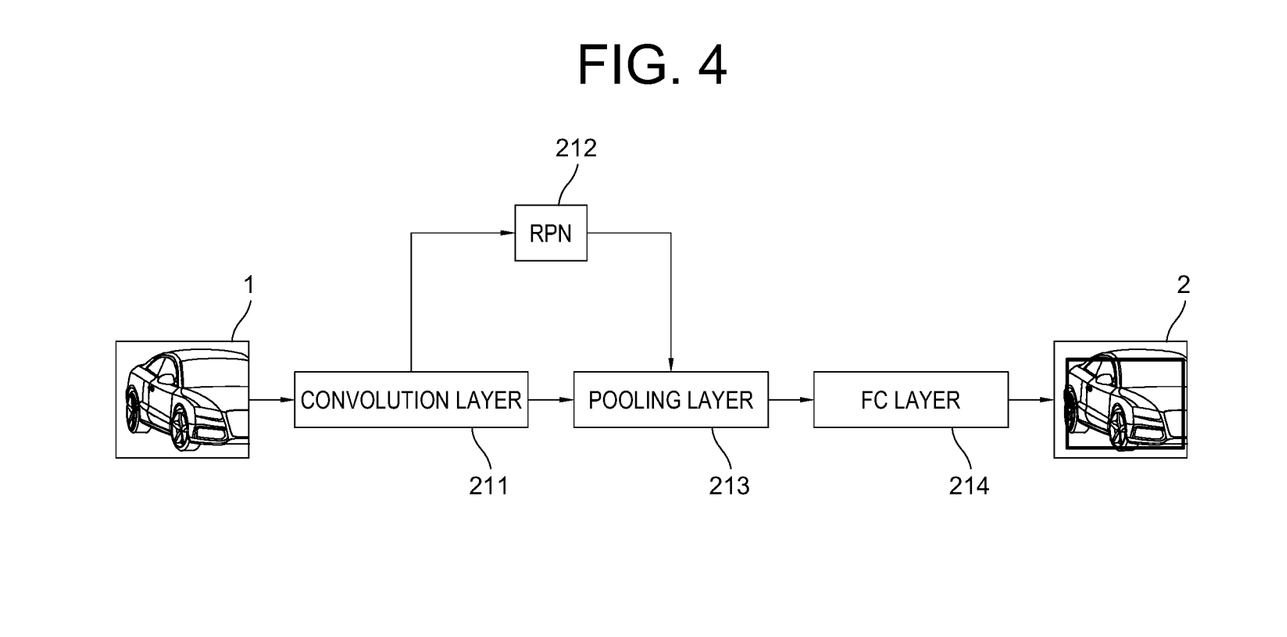
FIG. 4 is a drawing schematically illustrating the first object detector in the method for generating the object detector based on deep learning capable of detecting the extended object class in accordance with one example embodiment of the present disclosure.

Herein, referring to FIG. 4, in response to inputting a first source image 1, the first object detector 210 of FIG. 3 generates a feature map by performing one or more convolution operations on the first source image 1 through one or more convolution layers 211, generates ROIs which are regions where the first objects are predicted to be positioned in the feature map through RPN 212, generates pooled feature maps by cropping and resizing the regions corresponding to the ROIs in the feature map through a pooling layer 213, and outputs an object detection result 2 including bounding box information and object class information on each of the ROIs by performing one or more fully connected operations on the pooled feature maps through one or more FC layers 214.

Meanwhile, FIG. 4 above is one example of the first object detector for exemplarily explaining an R-CNN-based object detector, but the present invention is not limited thereto, and various object detectors based on deep learning such as YOLO(You Only Look Once), SSD (Single Shot multibox Detector), instance segmentation-based detector, etc. may be used.

Next, referring to FIG. 2 again, on condition that the first object detector has been trained to detect the first objects in the first input images containing at least one of the first objects by using the first training data set generated by annotation of the first object classes of the first objects in each of the first source images containing at least one of the first objects, the detector generation device 1000 may collect the second source images containing the one or more second objects corresponding to the second object classes, i.e., the extended class set, and then generate a second training data set by annotation of the second object classes of the second objects for each of the second source images at a step of S20.

As one example, the first source images of the first training data set are images collected for the first object classes, and thus a ratio of containing the second objects corresponding to the second object classes in the first source images is low, and accordingly, the number of the second objects contained in the first source images necessary for training the object detector capable of detecting the extended class set may not be sufficient. Accordingly, the detector generation device 1000 should collect the second source images including the one or more second objects corresponding to the second object classes and then transmit the collected second source images to one or more terminals of second labelers to thereby instruct the second labelers to annotate the second object classes for each of the second source images and to transmit the second training data set having the second object classes annotated through the second labelers to the detector generation device 1000.

Next, the detector generation device 1000 may generate a second object detector capable of detecting the second objects in the second input images through training processes using the second training data set. Herein, the second input images may be second images contained in the second training data set, or test images inputted to perform testing processes of the trained second object detector.

Figure 5:
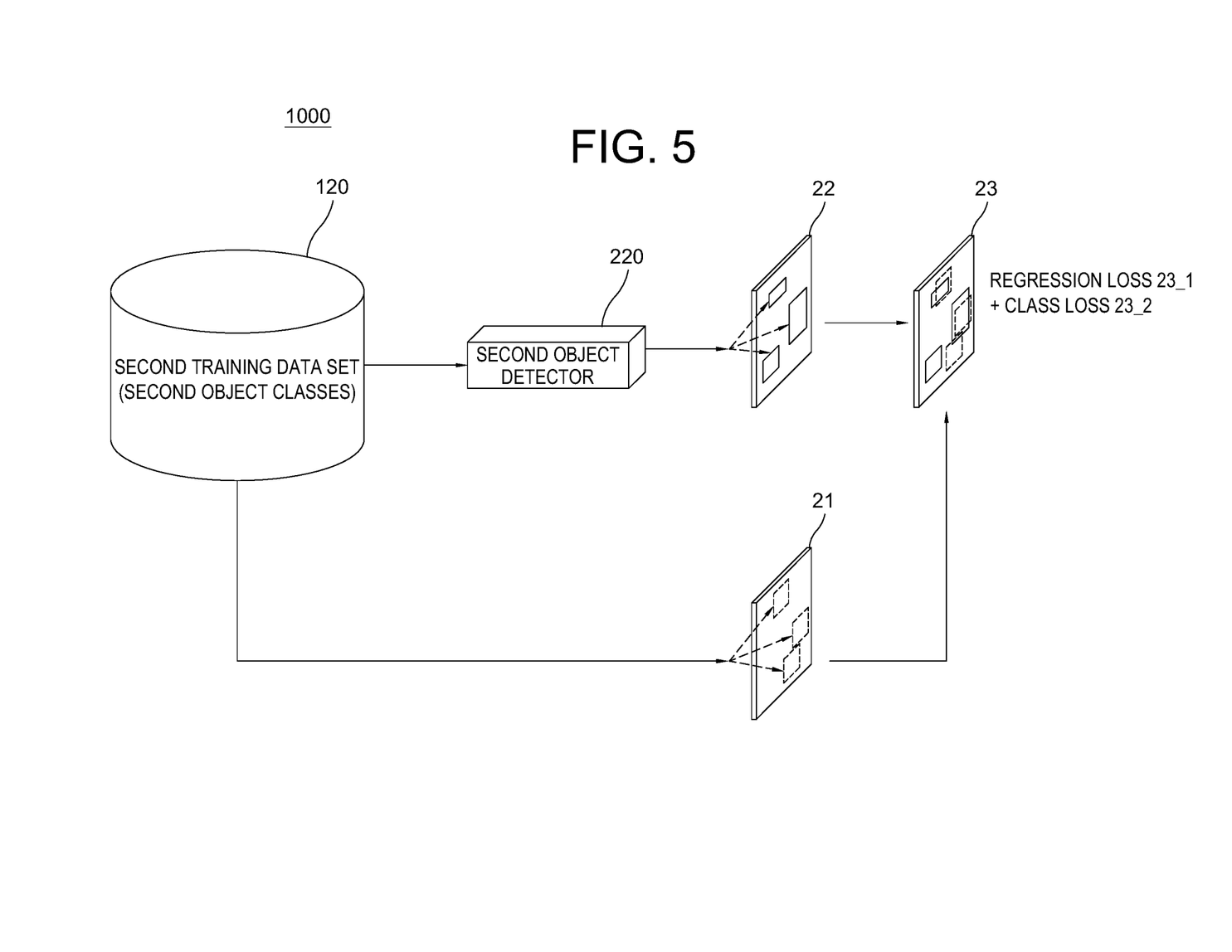
FIG. 5 is a drawing schematically illustrating a process of training a second object detector in the method for generating the object detector based on deep learning capable of detecting the extended object class in accordance with one example embodiment of the present disclosure.

As one example, referring to FIG. 5, on condition that the second training data set 120 containing the second source images annotated with the second object classes has been generated, the detector generation device 1000 may (i) input the second source images of the second training data set 120 to instruct a second object detector 220 having initialized weights, to thereby instruct the second object detector 220 to detect the second objects corresponding to the second object classes in each of the second source images, (ii) acquire (ii-1) regression losses 23_1 regarding positions of bounding boxes and class losses 23_2 regarding object classes of the bounding boxes by using (1) object detection results 22 acquired by detecting the second objects in each of the second source images through the second object detector 220 and (2) ground truths 21 for the second object classes annotated in each of the second source images, and (iii) update weights of the second object detector 220 to minimize the regression losses 23_1 and the class losses 23_2 by backpropagating them, to thereby generate the second object detector 220 having second weights.

Herein, an object detector having the initialized weights to be used for generating the second object detector 220 may be an object detector having an initialized weight used in generation of the first object detector or an object detector with trained weights, i.e., the first object detector having the initialized first weights.

Next, referring to FIG. 2 again, the detector generation device 1000 may generate a third training data set in which the first object classes and the second object classes are annotated by annotation of the second object classes corresponding to the second objects in each of the first source images with a reference to the second object detection results at a step of S40. Herein, the second object detection results are acquired by detecting the second objects contained in each of the first source images of the first training data set through the second object detector.

As one example, the detector generation device 1000 inputs each of the first source images of the first training data set into the second object detector with second weights having been trained to detect the second objects in the second input images, to thereby instruct the second object detector to detect the second objects in each of the first source images. Accordingly, the second object detector outputs the second object detection results acquired by detecting the second objects in each of the first source images through testing processes of the second object detector using the first source images. Herein, second object detection results may include pieces of class information and pieces of bounding box information for each of the second objects. Thereafter, the detector generation device 1000 may generate the third training data set in which the first object classes and the second object classes are annotated by annotation of the second object classes corresponding to the second objects detected in each of the first source images with a reference to the second object detection results. Herein, the second object detection results are acquired from each of the first source images. That is, unlike the conventional method which annotates the second object classes serving as the extended class set to each of the first source images through the labelers, the present invention can annotate the second object classes to the first source images by using the second object detection results detected in each of the first source images by using the second object detector trained to detect the second objects in the second input images, and thus time and cost for performing the annotation by the labelers are saved compared to the conventional method.

Next, the detector generation device 1000 may generate a fourth training data set in which the first object classes and the second object classes are annotated by annotation of the first object classes for the first objects detected in each of the second source images by referring to the first object detection results at a step of S50. Herein, the first object detection results are acquired by detecting the first objects contained in each of the second source images through the first object detector.

As one example, the detector generation device 1000 by inputs each of the second source images of the second training data set into the first object detector with the first weights having been trained to detect the first objects in the first input images, to thereby instruct the first object detector to detect the first objects in each of the second source images. Accordingly, the first object detector outputs the first object detection results acquired by detecting the first objects in each of the second source images through testing processes of the first object detector using the second source images. Herein, the first object detection results may include pieces of class information and pieces of bounding box information for each of the first objects. Thereafter, the detector generation device 1000 may generate the fourth training data set in which the first object classes and the second object classes are annotated by annotation of the first object classes corresponding to the first objects detected in each of the second source images by referring to the first object detection results. Herein, the first object detection results are acquired from each of the second source images. That is, unlike the conventional method which annotates the first object classes to each of the second source images through the labelers, the present invention can annotate the first object classes to the second source images by using the first object detection results detected in each of the second source images by using the first object detector trained to detect the first objects in the first input images, and thus time and cost for performing the annotation by the labelers are saved compared to the conventional method.

Next, the detector generation device 1000 may generate an integrated object detector trained to detect the first objects and the second objects in third input images by using the third training data set and the fourth training data set at a step of S60. Herein, the third input images are first images of the third training data set or second images of the fourth training data set, or test images inputted to perform testing processes of the trained integrated object detector.

Figure 6:
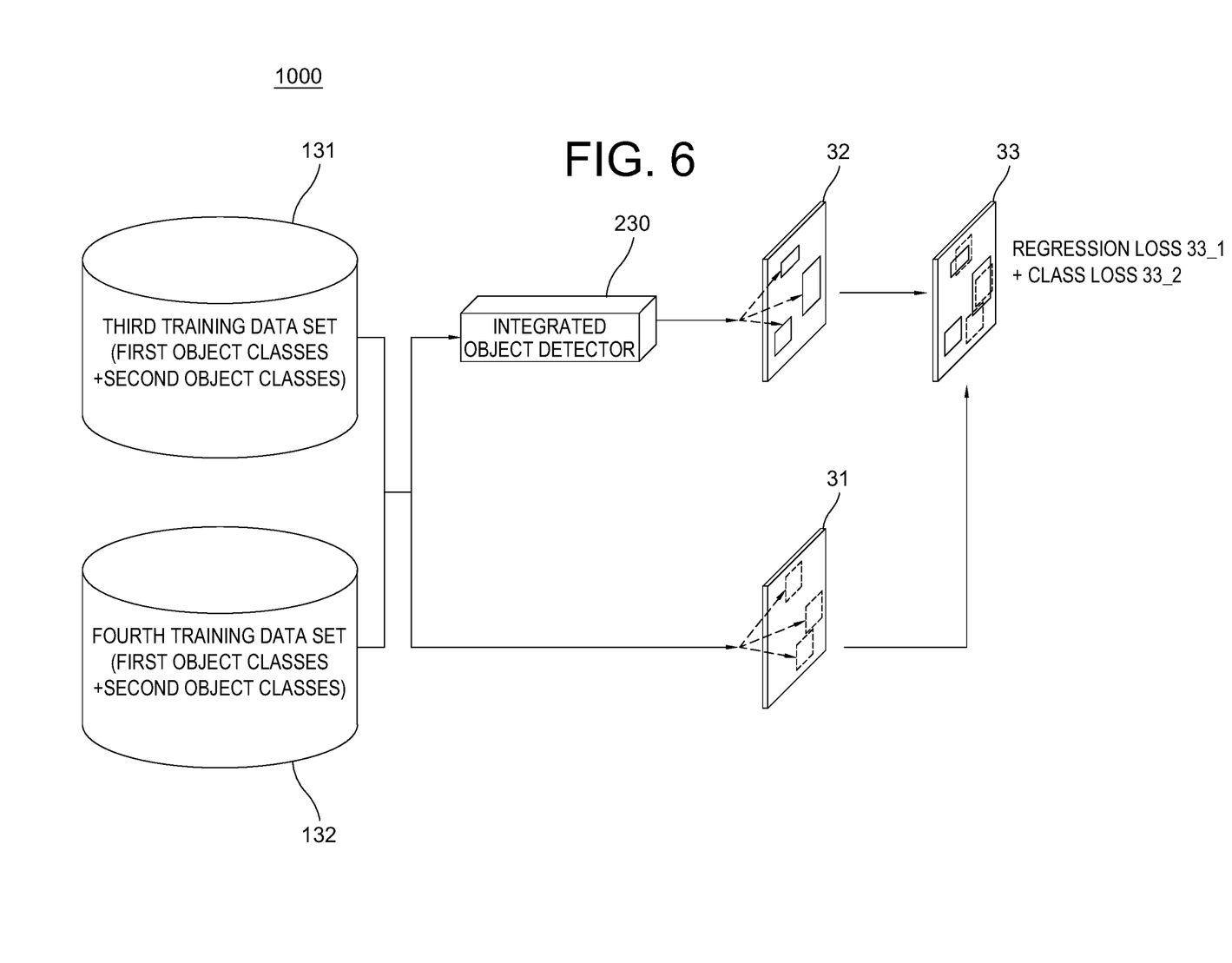
FIG. 6 is a drawing schematically illustrating a process of training an integrated object detector in the method for generating the object detector based on deep learning capable of detecting the extended object class in accordance with one example embodiment of the present disclosure.

As one example, referring to FIG. 6, on condition that a third training data set 131 in which the first object classes and the second object classes are annotated and a fourth training data set 132 in which the first object classes and the second object classes are annotated have been generated, the detector generation device 1000 may input the first images of the third training data set 131 and the second images of the fourth training data set 132 to an object detector having initialized weights, i.e., the integrated object detector 230 having initialized weights, to thereby instruct the integrated object detector 230 to detect the first objects corresponding to the first classes and the second objects corresponding to the second classes in each of the first images and the second images. Further, the integrated object detector 230 can acquire regression losses regarding positions of bounding boxes and class losses regarding object classes of the bounding boxes by using (1) object detection results 32 acquired by detecting the first objects and the second objects in each of the first source images and the second source images through the integrated object detector 230 and (2) ground truths 31 for the first object classes and the second object classes annotated in each of the first source images and the second source images, and then update weights of the integrated object detector 230 to minimize the regression losses 33_1 and the class losses 33_2 by backpropagating them, to thereby generate the integrated object detector 230 having the integrated weights.

Herein, an object detector having initialized weights used for generation of the integrated object detector 230 may be an object detector having initialized weights used in generation of the first object detector of the second object detector, or trained weights of the first object detector having the first weights, or trained weights of the second object detector having the second weights.

In addition, the detector generation device 1000 may generate the integrated object detector 230 by re-training the first object detector using the third training data set and the fourth training data set. Herein, the first object detector may be re-trained on condition that only some weights of a classifier predicting a class of an object contained in a bounding box have been initialized among the first weights of the first object detector.

In addition, the detector generation device 1000 may generate the integrated object detector 230 by re-training the second object detector 220 using the third training data set and the fourth training data set. Herein, the second object detector may be re-trained on condition that only some weights of a classifier predicting a class of an object contained in a bounding box have been initialized among the second weights of the second object detector.

The present disclosure has an effect of easily generating a training data set having an extended object class.

The present disclosure has another effect of minimizing an annotation cost for the extended object class.

The present disclosure has still another effect of minimizing an annotation time for the extended object class.

The present disclosure has still yet another effect of allowing to generate the training data set necessary for training an object detector capable of detecting the extended object class at a low cost in a short time.

The present disclosure has still yet another effect of allowing to generate the object detector capable of detecting the extended object class at a low cost in a short time.

Besides, the embodiments of the present disclosure as explained above can be implemented in a form of executable program command through a variety of computer means recordable to computer readable media. The computer readable media may store solely or in combination, program commands, data files, and data structures. The program commands recorded in the media may be components specially designed for the present disclosure or may be usable for a skilled human in a field of computer software. The computer readable media include, but are not limited to, magnetic media such as hard drives, floppy diskettes, magnetic tapes, memory cards, solid-state drives, USB flash drives, optical media such as CD-ROM and DVD, magneto-optical media such as floptical diskettes and hardware devices such as a read-only memory (ROM), a random access memory (RAM), and a flash memory specially designed to store and carry out program commands. Program commands may include not only a machine language code made by a compiler but also a high level code that can be used by an interpreter etc., which is executed by a computer. The aforementioned hardware device may work as more than a software module to perform the action of the present disclosure and they may do the same in the opposite case.

As seen above, the present disclosure has been explained by specific matters such as detailed components, limited embodiments, and drawings. While the invention has been shown and described with respect to the preferred embodiments, it, however, will be understood by those skilled in the art that various changes and modification may be made without departing from the spirit and scope of the invention as defined in the following claims.

What is claimed is:

1. A method for generating an object detector based on deep learning capable of detecting an extended object class, comprising steps of:
   (a) on condition that a first object detector is generated, wherein the first object detector has been trained to detect one or more first objects in a first input image by using a first training data set generated by annotation of first object classes of the first objects in each of first source images containing at least one of the first objects, in response to acquiring second source images containing one or more second objects, a detector generation device generating a second training data set by annotation of second object classes of the second objects for each of the second source images, and generating a second object detector trained to detect the second objects in a second input image by using the second training data set;
   (b) the detector generation device (i) (i-1) inputting the first source images of the first training data set into the second object detector, thereby instructing the second object detector to detect the second objects contained in each of the first source images and thus to output second object detection results, and (i-2) generating a third training data set containing the first source images in which the first object classes and the second object classes are annotated by annotation of the second object classes for the second objects detected in each of the first source images by referring to the second object detection results, and (ii) (ii-1) inputting the second source images of the second training data set into the first object detector, thereby instructing the first object detector to detect the first objects contained in each of the second source images and thus to output first object detection results, and (ii-2) generating a fourth training data set containing the second source images in which the first object classes and the second object classes are annotated by annotation of the first object classes for the first objects detected in each of the second source images by referring to the first object detection results; and
   (c) the detector generation device generating an integrated object detector trained to detect the first objects and the second objects in a third input image by using the third training data set and the fourth training data set.

2. The method of claim 1, wherein, at the step of (a), the detector generation device generates an object detector having initialized weights by initializing trained weights of the first object detector, and generates the second object detector by training the object detector having the initialized weights by using the second training data set.

3. The method of claim 1, wherein, at the step of (c), the detector generation device generates the object detector having initialized weights by initializing trained weights of the first object detector or by initializing trained weights of the second object detector, and generates the integrated object detector by training the object detector having the initialized weights by using the third training data set and the fourth training data set.

4. The method of claim 1, wherein, at the step of (c), the detector generation device generates the integrated object detector by re-training the first object detector using the third training data set and the fourth training data set.

5. The method of claim 1, wherein, at the step of (c), the detector generation device generates the integrated object detector by re-training the second object detector using the third training data set and the fourth training data set.

6. The method of claim 1, wherein, prior to the step of (a), the detector generation device transmits the first images to one or more first labeler terminals to thereby instruct the first labelers corresponding to the first labeler terminals to annotate the first object classes for each of the first images and instruct the first labelers to transmit the first images having the first object classes annotated through the first labeler terminals to the detector generation device, resulting in a generation of the first training data set.

7. The method of claim 1, wherein, at the step of (a), the detector generation device transmits the second images to one or more second labeler terminals to thereby instruct the second labelers corresponding to the second labeler terminals to annotate the second object classes for each of the second images and instruct the second labelers to transmit the second images having the second object classes annotated through the second labeler terminals to the detector generation device, resulting in a generation of the second training data set.

8. The method of claim 1, wherein the first object detector, the second object detector and the integrated object detector are generated by using an R-CNN-based object detector.

9. The method of claim 1, wherein the first object detector, the second object detector and the integrated object detector are generated by using an instance segmentation-based object detector.

10. A detector generation device for generating an object detector based on deep learning capable of detecting an extended object class, comprising:
at least one memory that stores instructions; and
at least one processor configured to execute the instructions to perform or support another device to perform processes of: (I) on condition that a first object detector is generated, wherein the first object detector has been trained to detect one or more first objects in a first input image by using a first training data set generated by annotation of first object classes of the first objects in each of first source images containing at least one of the first objects, in response to acquiring second source images containing one or more second objects, a detector generation device generating a second training data set by annotation of second object classes of the second objects for each of the second source images, and generating a second object detector trained to detect the second objects in a second input image by using the second training data set; (II) (i) (i-1) inputting the first source images of the first training data set into the second object detector, thereby instructing the second object detector to detect the second objects contained in each of the first source images and thus to output second object detection results, and (i-2) generating a third training data set containing the first source images in which the first object classes and the second object classes are annotated by annotation of the second object classes for the second objects detected in each of the first source images by referring to the second object detection results, and (ii) (ii-1) inputting the second source images of the second training data set into the first object detector, thereby instructing the first object detector to detect the first objects contained in each of the second source images and thus to output first object detection results, and (ii-2) generating a fourth training data set containing the second source images in which the first object classes and the second object classes are annotated by annotation of the first object classes for the first objects detected in each of the second source images by referring to the first object detection results; and (III) generating an integrated object detector trained to detect the first objects and the second objects in a third input image by using the third training data set and the fourth training data set.

11. The detector generation device of claim 10, wherein, at the process of (I), the processor generates an object detector having initialized weights by initializing trained weights of the first object detector, and generates the second object detector by training the object detector having the initialized weights by using the second training data set.

12. The detector generation device of claim 10, wherein, at the process of (III), the processor generates the object detector having initialized weights by initializing trained weights of the first object detector or by initializing trained weights of the second object detector, and generates the integrated object detector by training the object detector having the initialized weights by using the third training data set and the fourth training data set.

13. The detector generation device of claim 10, wherein, at the process of (III), the processor generates the integrated object detector by re-training the first object detector using the third training data set and the fourth training data set.

14. The detector generation device of claim 10, wherein, at the process of (III), the processor generates the integrated object detector by re-training the second object detector using the third training data set and the fourth training data set.

15. The detector generation device of claim 10, wherein, prior to the process of (I), the processor transmits the first images to one or more first labeler terminals to thereby instruct the first labelers corresponding to the first labeler terminals to annotate the first object classes for each of the first images and instruct the first labelers to transmit the first images having the first object classes annotated through the first labeler terminals to the detector generation device, resulting in a generation of the first training data set.

16. The detector generation device of claim 10, wherein, at the process of (I), the processor transmits the second images to one or more second labeler terminals to thereby instruct the second labelers corresponding to the second labeler terminals to annotate the second object classes for each of the second images and instruct the second labelers to transmit the second images having the second object classes annotated through the second labeler terminals to the detector generation device, resulting in a generation of the second training data set.

17. The detector generation device of claim 10, wherein the first object detector, the second object detector and the integrated object detector are generated by using an R-CNN-based object detector.

18. The detector generation device of claim 10, wherein the first object detector, the second object detector and the integrated object detector are generated by using an instance segmentation-based object detector.

* * * * *